United States Patent [19]

Cetenko et al.

[11] Patent Number: 5,464,856
[45] Date of Patent: Nov. 7, 1995

[54] ARYLMETHYLENYL DERIVATIVES OF IMIDAZOLIDINONES USEFUL AS ANTIINFLAMMATORY AGENTS

[75] Inventors: Wiaczeslaw A. Cetenko; David T. Connor; Roderick J. Sorenson; Paul C. Unangst, all of Ann Arbor, Mich.; Stephen R. Stabler, Santa Clara, Calif.

[73] Assignee: Warner-Lambert Company, Morris Plains, N.J.

[21] Appl. No.: 185,748

[22] Filed: Jan. 24, 1994

Related U.S. Application Data

[62] Division of Ser. No. 988,562, Dec. 10, 1992, Pat. No. 5,306,822, which is a division of Ser. No. 702,132, May 13, 1991, Pat. No. 5,208,250, which is a continuation of Ser. No. 375,794, Jul. 5, 1989, abandoned, which is a continuation-in-part of Ser. No. 334,346, Apr. 10, 1989, abandoned, which is a continuation-in-part of Ser. No. 198,528, May 25, 1988, abandoned.

[51] Int. Cl.$^6$ .................................................. A61K 31/415
[52] U.S. Cl. ........................................ 514/389; 548/317.1
[58] Field of Search .......................... 514/389; 548/317.1

[56] References Cited

FOREIGN PATENT DOCUMENTS 2169334 10/1973 France.
3023349 1/1982 Germany.
62-29570 2/1987 Japan.
2078218 1/1982 United Kingdom.

OTHER PUBLICATIONS

Patent Abstracts of Japan, vol. 10, No. 15, C–351, Jun., 1986, Abstract 61–12674.

*Primary Examiner*—Jacqueline Haley
*Attorney, Agent, or Firm*—Charles W. Ashbrook

[57] ABSTRACT

The present invention is for selected novel compounds, as well as, pharmaceutical compositions and methods of use for known and the selected novel compounds both of the formula

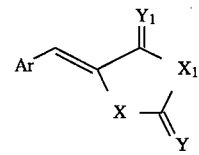

having activity useful for treating allergies and inflammation.

5 Claims, No Drawings

ARYLMETHYLENYL DERIVATIVES OF IMIDAZOLIDINONES USEFUL AS ANTIINFLAMMATORY AGENTS

This is a division of U.S. application Ser. No. 988,562 filed Dec. 10, 1992, now U.S. Pat. No. 5,306,822, which is a division of U.S. application Ser. No. 702,132 filed May 13, 1991, now U.S. Pat. No. 5,208,250, which is a continuation of U.S. application Ser. No. 375,794 filed Jul. 5, 1989, now abandoned, which is a continuation-in-part of U.S application Ser. No. 334,346 filed Apr. 10, 1990, now abandoned, which is a continuation-in-part of U.S. application Ser. No. 198,528 filed May 25, 1988, now abandoned.

BACKGROUND OF THE INVENTION

It is now found that compounds from among known and selected novel arylmethylenyl derivatives of thiazolidinones, oxazolidinones or imidazolidinones have activity useful for treating allergies or inflammation.

Thus, the present invention is for selected novel compounds, as well as, pharmaceutical compositions and methods of use for known compounds and the selected novel compounds of the formula (I)

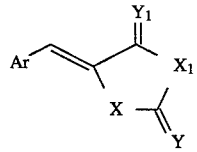

and pharmaceutically acceptable salts thereof; wherein Ar is (i) phenyl unsubstituted, (ii) phenyl substituted by from one to three of lower alkyl, lower alkoxy, hydroxy, halogen, trifluoromethyl, $NR_{10}R_{11}$ wherein $R_{10}$ and $R_{11}$ are independently hydrogen or lower alkyl, $NO_2$, mercapto, or lower alkylthio, (iii) naphthyl; (iv) benzofuranyl, (v) benzothiophenyl, (vi) 2— or 3-thienyl, (vii) 2- or 3-indolyl, (viii) 2- or 3-furanyl, or (ix) 2—, 3—, or 4-pyridyl Y and $Y_1$ l is oxygen or sulfur;

X is sulfur, oxygen, NH or $NCH_3$ and $X_1$ is NH or $NCH_3$ with the proviso that when Ar is substituted phenyl, the substitutents are either not 3,5-di(isopropyl)-4-hydroxy or if $X_1$= NH, X= S, Y= S not 3,5-di(t-butyl) together with 4-hydroxy.

Japanese Application No. 84-133826 as found in Derwent Abstracts No. 87-076379/11 discloses new 3,5-diisopropylbenzylidene-2,4-imidazolidinone and the analogous thiazoles with antiallergic and tyrosine kinase inhibiting activity as well as other heterocyclic containing compounds. EP No. 211,670A as described in Derwent 87-051809/08 describes compounds excluded by the proviso above having a 3,5-diisobutylbenzyledene substituent useful for treating inflammation, ischaemia induced cell damage and arthritis. Thus, known heterocyclic compounds are not as closely related as these named here and are excluded from the present invention.

A French Patent No. 2,169,334, C. H. Boehringer Sohn, Oct. 12, 1973 describes a series of N-substituted oxazoles as antiarthritics, antirheumatics, and immunosuppressants having the formula

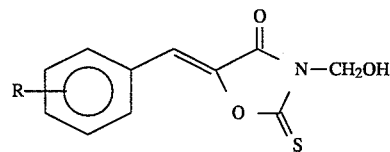

which are not included in the present invention.

Copending application PD-3518 is for novel compounds having a 3,5-di-tertiarybutyl-4-hydroxyphenyl moiety so its disclosure relating to references in the Background of the Invention is incorporated herein by reference.

The compounds of the formula I have a hitherto unknown pharmaceutical activity useful for treating allergic or inflammatory conditions or diseases. The invention compounds are now also found to have activity as inhibitors of 5-lipoxygenase and/or cyclooxygenase providing treatment of conditions advantageously affected by such inhibition including inflammation, arthritis, pain, pyrrhia, and the like. Thus, the present invention is also a pharmaceutical composition for diseases or conditions advantageously affected by activity inhibiting singly or together 5-lipoxygenase and cyclooxygenase or method of use therefor. Therefore, the present invention is particularly a pharmaceutical composition for the treatment of allergy or inflammation which comprises an antiallergy or antiinflammatory effective amount of a compound of the formula I together with a pharmaceutically acceptable carrier. Further, the present invention is a method for treating allergies or inflammation in subject suffering therefrom which comprises administering a compound of the formula I in unit dosage form.

The present invention is also the novel selected compounds of the formula I noted hereinafter having activity heretofore unknown for analogous compounds.

Among the known compounds for the compositions or methods of use of the present invention the following are referenced for compounds listed for the Examples of the invention:

| Example No. | Reference |
|---|---|
| 1 | J. Chem. Soc., pp. 958–65 (1946) |
| 2 | J. Org. Chem., 26, p. 1326 (1961) |
| 3 | Chem. Ber., pp. 459–69 (1941) |
| 4 | J. Chem. Soc., pp. 3547–52 (1950) |
| 5 | J.C.S., p. 1165 (1954) |
| 6 | J. Org. Chem., p. 1326 (1961) |
| 7 | U. S. Pat. No. 3,843,797/JACS, p. 2357 (1951) |
| 8 | C.A. 89: 100767m, JACS, p. 2357 (1951) |
| 9 | Tet., p. 2781 (1969) |
| 10 | Canadian J. Chem., p. 2089 (1959) |
| 12 | Ger. Pat. DE 3,433,475/C.A. 103, 928404 |
| 17 | J.O.C., p. 32 (1956) |
| 18 | Tet., p. 2781 (1969) |
| 19 | Tet., p. 2781 (1969) |
| 20 | Tet., p. 2781 (1969) |
| 21 | J. Ind. Chem. Soc., p. 77 (1984) |
| 22 | J. Ind. Chem. Soc., p. 77 (1984) |
| 26 | See Example 8 above |
| 28 | Int. J. Sulf. Chem. Part A, p. 261 (1972) |
| 29 | C.A. 76 (5), 25152h |
| 30 | C.A. 79 (25), 143522p |
| 32 | C.A. 76 (5), 25152h |
| 34 | C.A. 79 (25), 143522p |
| 36 | Biol. Mem. 9, 200 (1984) |
| 38 | Zh. Org. Khim, p. 212 (1983) |
| 40 | J.C.S. (1), p. 385 (1984) |
| 41 | C.A. 89: 100767n |

-continued

| Example No. | Reference |
|---|---|
| 42 | Chem. Phar. Bull., p. 1619 (1986) |
| 43 | Int. J. Sulf. Chem. Part A, p. 261 (1972) |
| 44 | J. Pharm. Soc. Jap., p. 154 (1956) |
| 45 | Ger. Pat. DE 3,433,475 |
| 48 | J.C.S., p. 3547 (1950) |
| 49 | C.A. 47, 9543a |
| 50 | C.A. 47, 9543a |
| 68 | C.A. 71 (17), 81253a |
| 69 | Zh. ob. Khim 26, p. 3092 (1956) |
| 71 | Ukrain Khim Zh. 16, p. 545 (1950) |
| 83 | Chem. Pharm. Bull., p. 1619 (1986) |
| 86 | Am. Chem. J., p. 368 (1911) |
| 87 | JACS, p. 1606 (1913) |
| 90 | JACS, p. 1606 (1913) |
| 91 | Monats, p. 352 (1961) |
| 92 | Chem. Pharm. Bull., p. 1619 (1986) |
| 96 | Roecz, Chem., p. 1381 (1984) |
| 103 | U. S. Pat. No. 3,017,270 |
| 104 | Egypt J. Chem., 26, 301 (1983) |
| 105 | French Pat. No. 1,604,530 |

The selected novel compounds of the present invention are found in Examples 11, 13–16, 51–53, 55–63, 64, 70, 72–79, 80, 82, 88, 97, and 99–101, 106–111.

Accordingly, the present invention is (a) a selected novel compound as in the noted examples heretofor or a salt thereof;

(b) a method for preparing a novel selected compound or a pharmacologically acceptable salt thereof;

(c) a pharmaceutical composition comprising a compound of formula (I) or a physiologically acceptable salt thereof and a pharmaceutically acceptable carrier therefor;

(d) a method for preparing such compositions;

(e) a method for the inhibition of histamine by use of a nontoxic, effective, inhibitory amount of a compound of formula I or a physiologically acceptable salt thereof;

(f) a method for the prophylaxis or treatment of disease or condition in a mammal, including man, comprising the administration to said mammal of a nontoxic, therapeutically or prophylactically effective amount of a compound of formula I or a physiologically acceptable salt thereof;

(g) a method for the prophylaxis or treatment of any individual condition described herein, in a mammal, including man, comprising the administration to said mammal of a nontoxic therapeutically or prophylactically effective amount of a compound of formula I or a physiologically acceptable salt thereof;

(h) a method for the prophylaxis or treatment of allergy or inflammatory condition in a mammal, including man, comprising administration to said mammal of a nontoxic, effective, antiallergic or antiinflammatory amount of a compound of formula I or a physiologically acceptable salt thereof;

(i) a novel compound as set out in the examples noted heretofor or a physiologically acceptable salt thereof for use in medicine, especially as defined in (f)–(h) above;

(j) use of a compound of formula I or a physiologically acceptable salt thereof in the manufacture of medical therapeutic agents, particularly those for use as defined in (f)–(h) above; and (k) any novel feature described herein.

SUMMARY OF THE INVENTION

The present invention is a pharmaceutical composition and method of use as defined above for compounds of the formula I as well as the novel compounds also as noted above.

A preferred embodiment of the present invention is the composition or method of use for a compound of the formula (II)

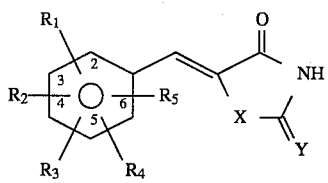

or pharmaceutically acceptable salts thereof; wherein X and Y are as defined above, $R_1$, $R_2$, $R_3$, $R_4$ and $R_5$ are independently H, lower alkyl, lower alkoxy, OH, halogen, $CF_3$, $NR_{10}R_{11}$ wherein $R_{10}$ and $R_{11}$ are as defined above, $NO_2$, mercapto, or lower alkylthio, wherein of from one to three of $R_1$, $R_2$, $R_3$, $R_4$, and $R_5$ are other than hydrogen, but excluding $R_1$, $R_2$, $R_3$, $R_4$ and $R_5$ which are 3,5-di(2-isopropyl) and 4-OH or which are 3,5-di(t-butyl) and 4-OH when X is NH, or both X and Y are S.

A preferred embodiment of the formula II of the present invention is the composition or method of use for a compound of the formula (III)

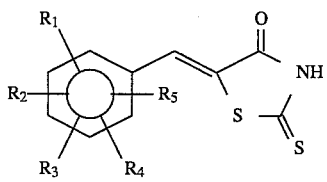

or pharmaceutically acceptable salts thereof; wherein $R_1$, $R_2$, $R_3$, $R_4$ and $R_5$ are as defined above.

Another preferred embodiment of the formula I I of the present invention is the composition or method of use for a compound of the formula (IV)

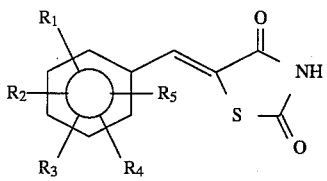

or pharmaceutically acceptable salts thereof; wherein $R_1$, $R_2$, $R_3$, $R_4$ and $R_5$ are as defined above.

Also among the preferred embodiment of the formula II is the composition and method of use for the compound of the formula (V)

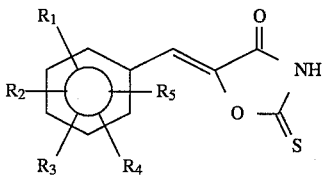

or pharmaceutically acceptable salts thereof; wherein $R_1$, $R_2$, $R_3$, $R_4$ and $R_5$ are as defined above.

Another preferred embodiment of the formula II is the composition and method of use for the compound of the formula (VI)

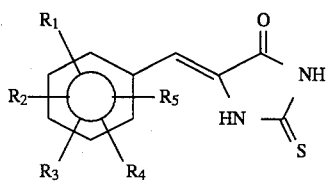

or pharmaceutically acceptable salts thereof; wherein $R_1$, $R_2$, $R_3$, $R_4$ and $R_5$ are as defined above.

Another preferred embodiment of the formula II is the composition and method of use for the compounds of the formula (VII)

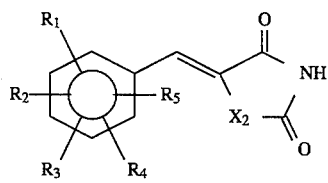

or pharmaceutically acceptable salts thereof; wherein $X_2$ is NH or $NCH_3$ and $R_1$, $R_2$, $R_3$, $R_4$ and Rs is as defined above.

Another preferred embodiment of the formula II is the composition and method of use for the compounds of the formula (VIII)

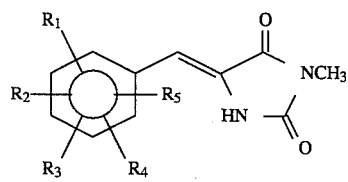

or pharmaceutically acceptable salts thereof wherein $R_1$, $R_2$, $R_3$, $R_4$, and $R_5$ are as defined above. And finally, a preferred embodiment of the formula II is the composition and methods of use for the compounds of the formula VIIIA

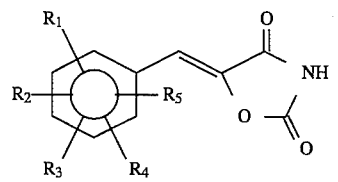

or pharmaceutically acceptable salts thereof; wherein $R_1$, $R_2$, $R_3$, $R_4$ and $R_5$ are as defined above.

The most preferred embodiment of the formula II is the composition and method of use for the following compounds which inhibit the release of histamine from human basophils as described hereinafter in the HHB assay stimulated with anti IgE at an $IC_{50}$ less than 20 μM.

5-[(2,5-dimethoxyphenyl)methylene]-2-thioxo-4-thiazolidinone,

5-[2,4,5-trimethoxyphenyl)methylene]-2-thioxo-4-thiazolidinone,

5-[(3,4,5-trimethoxyphenyl)methylene]-2-thioxo-4-thiazolidinone,

5-[(3,4-dichlorophenyl)methylene]-2-thioxo-4-thiazolidinone,

5-[(3,4-dimethoxyphenyl)methylene]-2-thioxo-4-thiazolidinone,

5-[(3,5-dimethoxy-4-hydroxyphenyl)methylene)-2-thioxo-4-thiazolidinone,

5-[(3,5-dimethyl-4-hydroxyphenyl)methylene)-2-thioxo-4-thiazolidinone,

5-[(5-bromo-4-hydroxy-3-methoxyphenyl)methylene)-2-thioxo-4-thiazolidinone,

5-[(4-methoxyphenyl)methylene]-2-thioxo-4-thiazolidinone,

5-[(5-hydroxy-4-methoxyphenyl)methylene)-2-thioxo-4-thiazolidinone,

5-[(3,5-dimethoxyphenyl)methylene]-2-thioxo-4-thiazolidinone,

5-[(4-hydroxy-3,5-dimethoxyphenyl)methylene]2,4-thiazolidinedione,

5-[(4-hydroxy-3-methoxyphenyl)methylene]-2,4-thiazolidinedione,

5-[(4-hydroxy-3-methoxyphenyl)methylene]-2-thioxo-4-oxazolidinone,

5-[(4-hydroxy-3,5-dimethoxyphenyl)methYlene]-2-thioxo-4-oxazolidinone, 2-thioxo-5-[(3,4,5-trimethoxyphenyl)methYlene]-4-oxazolidinone, 5-[(4-hydroxy-3,5-dimethoxyphenyl)methYlene]-2-thioxo-4-imidazolidinone.

Novel compounds which inhibit singly or together 5-lipoxygenase and cyclooxygenase are found by determining percent inhibition in ARBL/ARBC Whole Cell 5-lipoxygenase and Cyclooxygenase Assays and Carrageenan-Induced Rat Foot Paw Edema-2 (CFE-2) Assay described hereinafter.

Among the preferred compounds as determined in the ARBL/ARBC and CFE-2 assays are the following:

2,4-thiazolidione, 5-[[3,5-bis(1,1-dimethylethyl)-4-hydroxyphenyl] methylene]-, (E)-

4-oxazolidinone, 5-[[3,5-bis(1,1-dimethylethyl)-4-hydroxyphenyl] methylene]-2-thioxo- 2,4-oxazolidinone, 5-[[3,5-bis(1,1-dimethylethyl)-4hydroxyphenyl] methylene]-, 2,4-oxazolidinedione, 5-[(4-hydroxy-3,5-dimethoxyphenyl)methylene] -, and 4-thiazolidinone, 5-[(4-bromophenyl)methylene]-2-thioxo-.

The most preferred novel compound of the present invention now found having activity which inhibits 5-lipoxygenase and cyclooxygenase are 5-[[3,5-bis(1,1-dimethylethyl)-4-hydroxyphenyl] methylene]-2,4-thiazolidinedione and 5-[(3,5-bis(1,1-dimethylethyl)-4-hydroxyphenyl]-2-thioxo-4oxazolidinone.

Thus, the present invention is also a pharmaceutical composition for the treatment of conditions advantageously affected by the inhibition of 5-lipoxygenase and/or cyclooxygenase which comprises an amount effective for the treatment of the condition of a compound of the formula I or various preferred embodiments and the pharmaceutically acceptable acid addition or base salt thereof together with a pharmaceutically acceptable carrier. The condition is meant to include, for example, arthritis or other inflammatory diseases, allergic conditions or diseases, pain, fever, and psoriasis, but now preferably inflammatory diseases.

The present invention is also a method for treatment of the condition as noted above in a mammal, including humans, suffering therefrom with a compound of the formula I or the pharmaceutically acceptable acid addition or base salt thereof, in unit dosage form. The invention also provides for use of any such compound of formula I or particularly various preferred embodiments or salt thereof in the manufacture of medical therapeutic agent.

Pharmaceutical composition or use of the compound or salt of formula I is meant to include treatment understood to be prophylactic pertinent to the foregoing named condition.

A DETAILED DESCRIPTION OF THE INVENTION

In the present invention "lower alkyl" is alkyl of from one to six carbons, inclusive, and means methyl, ethyl, propyl, butyl, pentyl, or hexyl and isomers thereof.

"Lower alkoxy" means methoxy, ethoxy, propoxy, butoxy, pentoxy, or hexoxy and isomers thereof.

"Lower alkylthio" means methylmercapto, ethylmercapto, propylmercapto, butylmercapto, pentylmercapto, or hexylmercapto and isomers thereof.

"Halogen" is chloro, bromo, fluoro, or iodo.

Generally, the selected novel compounds of formula I as well as the known compounds are prepared by processes that are known or are prepared by processes analogous to those that are known from known starting materials or starting materials that can be prepared by known methods. For example, the following starting materials are obtained as follows:

3-Bromo-4-hydroxybenzaldehyde and 3,5-dibromo-4-hydroxybenzaldehyde are prepared according to Paal, *Chem. Ber.* 28 (1895), 2407.

4,5-Dimethoxy-2-hydroxybenzaldehyde is prepared according to Robinson & Head, *J. Chem. Soc.* (1930), 2440.

Scheme 1

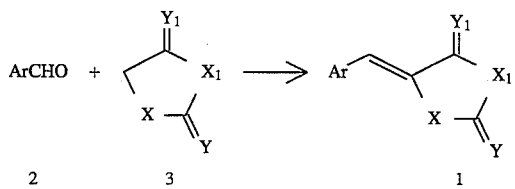

wherein Ar, $X_1$, X and Y are as defined above.

More particularly, the present invention includes compounds of type 1:

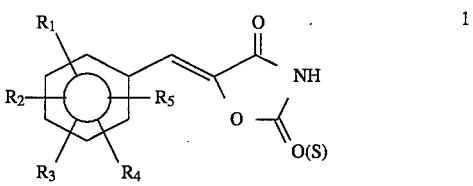

where $R_1$, $R_2$, $R_3$, $R_4$, and $R_5$ are as defined above. These compounds are named as substituted 5-phenylmethylene-2-thioxo-4-oxazolidinones, or 5-phenylmethylene-2,4-oxazolidedones.

Certain thiazolidinones and oxazolidinones are acidic (pKa~ 3–6) due to the presence of a tautomeric proton on the heterocyclic ring:

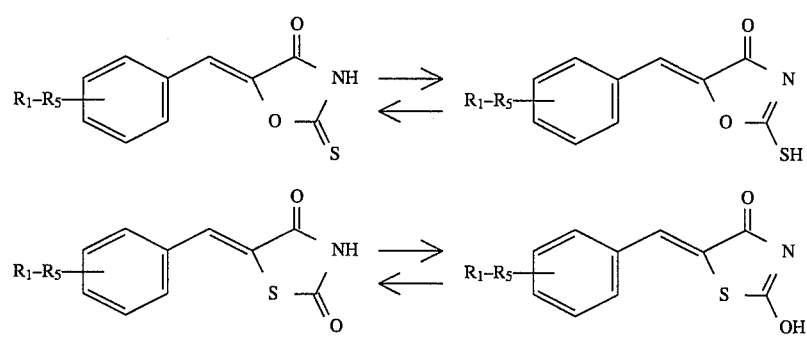

3-Methoxy-5-hydroxybenzaldehyde is prepared according to Ben, et. al., *J. Org. Chem.* 50 (1985), 2238.

3,5-Diisopropyl-4-hydroxybenzaldehyde and 3,5-dimethyl 4-hydroxybenzaldehyde are prepared according to U.S. Pat. No. 4,009,210.

3-(dimethylamino)methyl-4-hydroxy-5-methoxybenzaldehyde is prepared according to Hemetsberger, *Monats. Chem.* 102 (1971), 1110.

3-Methylhydantoin is prepared according to Galer and Moodie, *J. Chem. Soc. Perk II* (1980), 1752.

A scheme for preparation of the compounds of formula I above is as follows:

These compounds can form salts with inorganic and organic bases, including choline derivatives.

If the parent oxazolidinone or thiazolidinone and choline free base or a choline derivative (such as choline bicarbonate or choline chloride) are combined in a suitable solvent (such as an alcohol, water, or an alcohol/water solution), the choline salt can generally be obtained by precipitation from solution or by evaporation of the reaction solution.

A general method of preparation of these compounds is the aldol condensation of an aldehyde 2 with an active methylene compound 3 (Scheme 1 above). This condensation can be carried out in alcoholic solvents in the presence of a base such as ammonia, ammonium salts, or piperidine, or with mineral acid

Scheme 1'

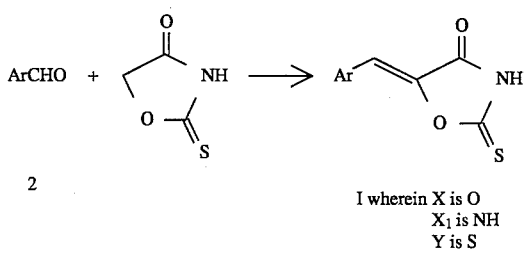

I wherein X is O
X₁ is NH
Y is S catalysis. A particularly favored procedure is the use of anhydrous sodium acetate in glacial acetic acid, with heating at reflux for 1-24 hours. References to this procedure include: G. R. Newkome and A. Nayak, in Advances in Heterocyclic Chemistry, A. R. Katritzky and A. J. Boulton, Eds., Academic Press, New York, N.Y., Vol. 25, p. 83 and N. K. Ushenko and T. E. Gorizdra, Ukrain Khim. Zhur., 16, 545 (1950).

An alternate procedure for the preparation of the above compound when Y=O is the preparation of the corresponding oxazole 4 followed by oxidation/hydrolysis to the desired oxazole I wherein X is O, X₂ is NH and Y is O (Scheme 2):

Scheme 2

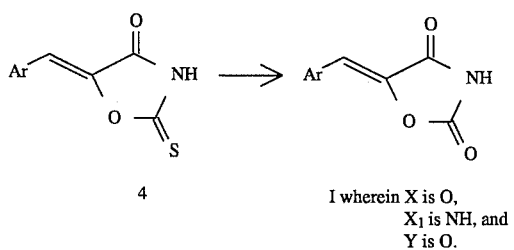

4

I wherein X is O,
X₁ is NH, and
Y is O.

For the preparation of 4, see, for example, F. C. Brown, *Chem. Rev.*, 61, 463 (1961), and the (Newkome) reference previously cited. For the conversion 4 to I of Scheme 2, see also J. W. Clark-Lewis, *Chem. Rev.*, 58, 63 (1958), and N. A. Shenberg, L. S. Guseva, A. I. Ginak, and E.G. Sochilin, *Zhur. Organ. Khim.*, 14, 1323 (1978).

Variations of the above Scheme 1 are also readily prepared by the methods of Scheme 1" discussed above. These are shown here in Scheme 1 " as follows.

Scheme 1"

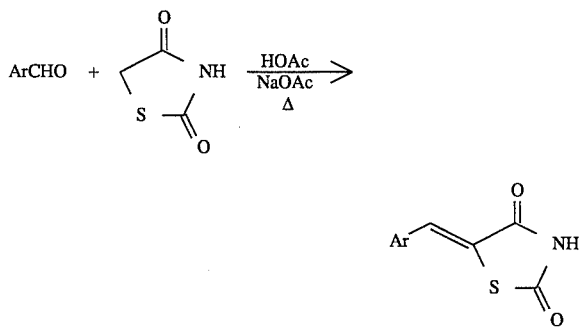

and

-continued
Scheme 1"

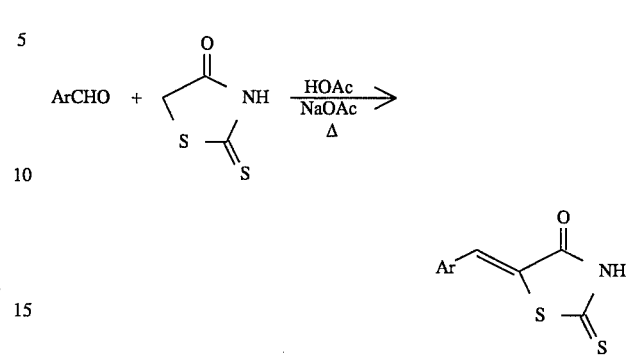

An alternate procedure for the preparation of the above noted oxazole I wherein X is O, X₁ is NH, and Y is O is by an alkylation/hydrolysis procedure ( Scheme 2 ) as follows:

Scheme 2'

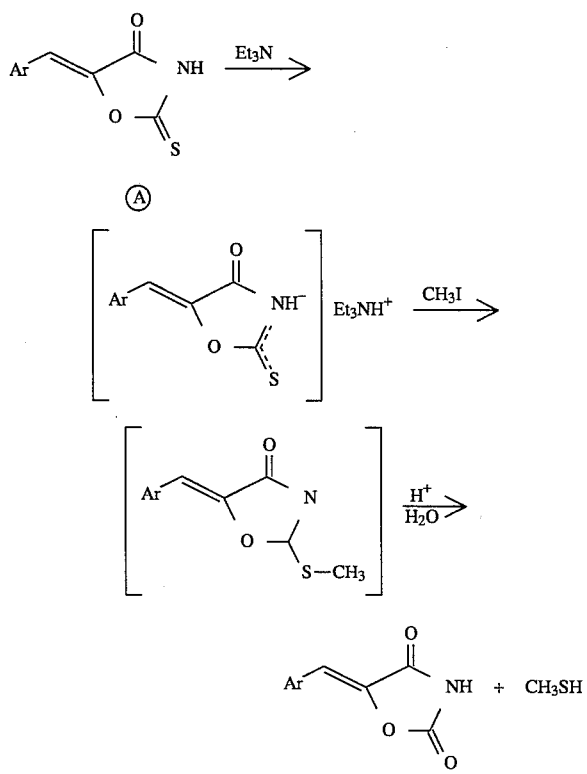

The procedure of Scheme 2' is essentially that of N. A. Shenberg, L. S. Guseva, A. I. Ginak, and E.G. Sochilin, *Zhur. Organ. Khim.*, 14, 1323 (1978); and J. S. H. Davies, W. Hook, and F. Long, *J. Chem. Soc.*, 30 (1950).

The compounds of formula I are useful both in the free acid form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methylglucosamine; N-methylpiperazine; morpholine; ethylenediamine; N-benzylphenethylamine; tris(hydroxymethyl) aminomethane; and the like. (See for example, "Pharmaceutical Salts," *J. Pharm. Sci.*, 66(1), 1–19 (1977).)

The acid addition salts of said basic compounds are prepared either by dissolving the free base of compound I in aqueous or aqueous alcohol solution or other suitable solvents containing the appropriate acid or base and isolating the salt by evaporating the solution, or be reacting the free base of compound I with an acid as well as reacting compound I having an acid group thereon with a base such that the reactions are in an organic solvent, in which case the salt separates directly or can be obtained by concentration of the solution.

The base salts of compounds of formula I described above are prepared by reacting the appropriate base with a stoichiometric equivalent of the acid compounds of formula I to obtain pharmacologically acceptable base salts thereof.

The acid solution salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may also exist in hydrated or solvated forms.

The products of the reactions described herein are isolated by conventional means such as extraction, distillation, chromatography and the like.

The antiallergic and antiinflammatory activity of the compounds having the formula I of the present invention is determined by an assay showing inhibition of the release of histamine from human basophils (HHB). A description of the protocol of the HHB assay is found hereinafter.

Thus, pharmaceutical compositions are prepared from the compounds of formula I and salts thereof described as the present invention in unit dosage form comprising the compound either alone or in admixture with a pharmaceutically acceptable carrier appropriately selected from those known.

A physician or veterinarian of ordinary skill readily determines a subject who is exhibiting allergic or inflammatory symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area (e.g., in the form of eye drops or by inhalation). For the treatment of allergic or inflammatory conditions such as erythema, the compounds of the present invention may also be administered topically in the form of ointments, creams, gels, or the like. In general, the preferred route of administration is orally.

An effective but nontoxic quantity of the compound I is employed in treatment. The ordinarily skilled physician or veterinarian will readily determine and prescribe the effective amount of the antiallergic or antiinflammatory agent to prevent or arrest the progress of the condition. The dosage regimen is selected in accordance with a variety of factors including the type, age, weight, sex, and medical condition of the mammal, the severity of symptoms of the disease being treated, the route of administration and particular compound of formula I employed. An ordinarily skilled physician or veterinarian will readily determine and prescribe the effective amount of the compound I to prevent or arrest the progress of the condition. In so proceeding, the physician or veterinarian could employ relatively low dosages at first, subsequently increasing the dose until a maximum response is obtained. For convenience, the total daily dosage may be divided and administered in portions during the day if desired. In so proceeding, the physician or veterinarian could employ relatively low dosages at first, subsequently increasing the dose until a maximum response is obtained.

Initial dosages of the compounds of the invention having formula I are ordinarily in the area of 10 mg up to 2 g per day orally, preferably 20 mg to 500 mg per dose orally, given from one to four times daily or as needed. When other forms of administration are employed, equivalent doses are administered.

A suitable dose of a compound of formula (I) or pharmacologically acceptable salt thereof for a mammal suffering from, or likely to suffer from any condition as described hereinbefore is 0.1 µg–500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 mg–100 µg of the compound per kilogram, typically about 0.1 µg/kg.

In the case of oral dosing for the treatment or prophylaxis of arthritis or inflammation in general, due to any course, a suitable dose of a compound of formula (I) or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg.

It is understood that the compositions and methods of treatment of the present invention as described above also include the free acid, the pharmacologically acceptable base salts and acid addition salts of the compounds of formula I.

The following Examples further illustrate the invention, but are not meant to be limiting thereto.

EXAMPLE 1

5-[(2,3-Dimethoxyphenyl)methylene]-2-thioxo-4-thiazolidinone

A mixture of 2,3-dimethoxybenzaldehyde (5.2 g, 30 mmoles), rhodanine (4.0 g, 29 mmoles), sodium acetate (8.4 g, 102 mmoles), and acetic acid (50 ml) is stirred under an inert atmosphere and heated to reflux. After 4 hours the mixture is stirred into water (250 ml) and the precipitate is filtered off, rinsed successively with water (3X), ethanol (2X), and ether (2X), and dried to afford the pure product (7.8 g), mp 268°–269° C.

The following examples are prepared from the corresponding benzaldehydes using the procedure described in Example 1.

TABLE 1

[Structure: benzene ring with substituents $R_1$ (top), $R_2$, $R_3$, $R_4$, connected via CH=C to thiazolidinone ring with NH, C=O, S, C=S]

| Example | $R_1$ | $R_2$ | $R_3$ | $R_4$ | mp °C. | |
|---|---|---|---|---|---|---|
| 2 | OMe | H | OMe | H | 275–276 | |
| 3 | OMe | H | H | OMe | 245–246 | |
| 4 | OMe | OMe | OMe | H | 205–206 | |
| 5 | OMe | H | OMe | OMe | 297 (dec) | |
| 6 | H | OMe | OMe | OMe | 200–201 | |
| 7 | Cl | H | Cl | H | 234–235 | (Recryst. from DMF) |
| 8 | H | Cl | Cl | H | 241–242 | |
| 9 | H | OMe | OMe | H | 232–234 | |
| 10 | H | OMe | OH | OMe | 252–253 | (Recryst. from MeOH) |
| 11 | H | F | OMe | H | 264–265 | |
| 12 | H | OH | OH | H | >300 | |
| 13 | H | Br | OH | H | 283–285 | (Recryst. from EtOH) |
| 14 | H | Br | OH | Br | >300 | |
| 15 | H | Me | OH | Me | 293–295 | |
| 16 | H | OMe | OH | Br | 275 (dec) | |
| 17 | H | H | H | H | 204–205 | |
| 18 | MeO | H | H | H | 249–250 | |
| 19 | H | MeO | H | H | 232–233 | |
| 20 | H | H | MeO | H | 250–251 | |
| 21 | H | OH | H | H | 246–248 | |
| 22 | H | H | OH | H | 288 (dec) | |
| 23 | H | OEt | H | H | 170–172 | |
| 24 | H | OCHMe$_2$ | H | H | 191–193 | |
| 25 | H | OCH$_2$Ph | H | H | 197–198 | |
| 26 | H | Me | H | H | 198–200 | |
| 27 | H | CF$_3$ | H | H | 189–190 | |
| 28 | H | Cl | H | H | 233–235 | |
| 29 | H | Br | H | H | 239–241 | |
| 30 | H | NO$_2$ | H | H | 265–267 | |
| 31 | H | H | Cl | H | 224–226 | |
| 32 | H | H | Br | H | 236–238 | |
| 33 | H | H | OPh | H | 150–151 | |
| 34 | H | H | NO$_2$ | H | 265–267 | |
| 35 | H | H | SMe | H | 258–260 | |
| 36 | H | MeO | OH | H | 229–230 | |
| 37 | H | MeO | H | MeO | 257–259 | |
| 38 | H | H | Me | H | 225–227 | |
| 39 | H | H | Ph | H | 240–242 | |

EXAMPLE 40

5-[(2,3-Dichlorophenyl)methylene]-2-thioxo-4-thiazolidinone

A mixture of 2,3-dichlorobenzaldehyde (4.6 g, mmoles), rhodanine (3.5 g, 25 mmoles), sodium acetate (7.5 g, 91 mmoles), and acetic acid (40 ml) is stirred under an inert atmosphere and heated to reflux. After 2.5 hours the mixture is stirred into ice-water (250 ml) and the precipitate is filtered off, rinsed three times with water and dried. Recrystallization from methanol gave the pure product (2.9 g), mp 203°–204° C.

The following examples are prepared from the corresponding benzaldehyes using the procedure described in Example 40:

| Example | $R_1$ | $R_2$ | $R_3$ | $R_4$ | $R_5$ | mp °C. | Recryst. Solvent |
|---|---|---|---|---|---|---|---|
| 41 | Cl | H | H | H | Cl | 179–181 | — |
| 42 | H | tBu | OH | tBu | H | 248–249 | EtOAc |
| 43 | H | F | H | H | H | 201–202 | MECN |
| 44 | H | OH | H | H | H | 216 (dec) | MECN |
| 45 | H | OH | OMe | H | H | 224–225 | MEOH |
| 46 | H | iPr | OH | iPr | H | 200–202 | MECN |
| 47 | H | OH | OMe | OMe | H | 212–213 | MEOH |
| 48 | H | OMe | H | H | OMe | 273–275 | DMF |
| 49 | OH | H | H | OMe | H | 253 (dec) | — |
| 50 | H | OH | H | OMe | H | 259–260 | THF |
| 51 | H | OMe | OH | tBu | H | 233–234 | MECN |
| 52 | OH | H | OMe | OMe | H | 258 (dec) | |

EXAMPLE 53

5-[[3-[(Dimethylamino)methyl]-4-hydroxy-5-methoxyphenyl] methylene]-2-thioxo-4-thiazolidinone A mixture of 3-[(dimethylamino)methyl]-4-hydroxy-5-methoxybenzaldehyde (2.5 g, 12 mmoles), rhodanine (1.6 g, 12 mmoles), β-alanine (0.6 g, 7 mmoles), and acetic acid (35 ml) is stirred under an inert atmosphere and heated to reflux. After 4 hours the acetic acid is removed by rotary evaporator and the residue dissolved in water (250 ml). The solution is brought to approximate neutrality by addition of saturated aqueous sodium bicarbonate, and stirred for 3 hours. The precipitate is filtered off, rinsed three times with water and dried, then triturated in boiling methanol (100 ml), cooled, filtered off and dried to afford the pure product (2.9 g), mp 198° C. (dec).

EXAMPLE 54

5-[(5-Bromo-2-thienyl)methylene]-2-thioxo-4-thiazolidinone

Prepared by the method described in Example 1 from 5-bromo-2-thiophenecarboxaldehyde, mp 250°–252° (dec).

INTERMEDIATE A

N,6-Dimethoxy-N-methyl-2-benzofurancarboxamide

To a stirred solution of 6.0 g (0,031 mole) of 6-methoxy-2-benzofurancarboxylic acid (A. McGookin, A. Robertson, and W. B. Whalley, *J. Chem. Soc.* 787 (1940)) in 100 ml of tetrahydrofuran (under a nitrogen atmosphere) was added in one portion, 3.3 ml (4.8 g; 0,038 mole) of oxalyl chloride. The mixture was stirred for 5 minutes, then treated with 3 drops of N,N-dimethylformamide. After stirring at room temperature for 2 hours, the solvent was evaporated to leave a residue of crude 6-methoxy-2-benzofurancarbonyl chloride, mp 96°–99° (amp of 101° is given by A. McGookin, etc., cited above). The residue was re-dissolved in 100 ml of dichloromethane, and the solution was filtered. The filtrate was added dropwise over 20 minutes to an ice-cooled solution of 3.6 g (0,037 mole) of N,)-dimethylhydroxylamine hydrochloride and 9.4 ml (7.7 g; 0,077 mole) of 1-methylpiperidine in 100 ml of dichloromethane. After stirring for 2 hours, the mixture was added to 400 ml of ice-cold 5% aqueous hydrochloric acid. The layers were separated, and the aqueous layer was extracted with fresh dichloromethane (3X 100 ml). The combined organic layers were washed with water (1X 200 ml), 3% aqueous sodium bicarbonate (2X 200 ml), and water again. The extracts were dried (anhydrous magnesium sulfate) and evaporated. Trituration of the residue with ether yielded 5.4 g (74% yield) of the analytically pure amide product, mp 73°–77°.

Calcd. for $C_{12}H_{13}NO_4$:
C, 61.27;H, 5.57; N, 5.96
Found: C, 61.26;H, 5.52; N, 5.78.

INTERMEDIATE B

6-Methoxy-2-benzofurancarboxaldehyde

An ice-cooled solution of 4.0 g (0.017 mole) of N,6-dimethoxy-N-methyl-2-benzofurancarboxamide in 100 ml of tetrahydrofuran was treated cautiously over 15 minutes (under a nitrogen atmosphere) with 0.65 g (0.017 mole) of lithium aluminum hydride. The mixture was stirred for 1 hour, then quenched by the careful addition of 100 ml of saturated aqueous sodium bisulfate solution. The reaction mixture was extracted with ether (3X 75 ml), and the combined extracts were washed with cold 2% aqueous hydrochloric acid (2X 100 ml), followed by brine (1X 100 ml). The organic layer was dried (anhydrous magnesium sulfate) and evaporated. The residue was chromatographed (silica gel, dichloromethane elution) to yield 2.2 g (74% yield) of the analytically pure aldehyde, mp 75°–77°.

Calcd. for $C_{10}H_8O_3$:
C, 68.18; H, 4.58
Found: C, 68.03, H, 4.48.

EXAMPLE 55

5-[(6-Methoxy-2-benzofuranyl)methylene]-2-thioxo-4-thiazolidinone

A mixture of 1.5 g (0.0085 mole) of 6-methoxy-2-benzofurancarboxaldehyde, 1.1 g (0.0083 mole) of 2-thioxo-4-thiazolidinone ("rhodanine"), and 2.5 g (0.030 mole) of anhydrous sodium acetate in 40 ml of glacial acetic acid (under a nitrogen atmosphere) was stirred and heated at reflux for 5 hours. The cooled mixture was added to 250 g of ice/water. The precipitated solid was filtered, washed with water, then with a little cold ethanol to yield 2.0 g (81% yield) of the analytically pure thiazole, mp > 290°.

Calcd. for $C_{13}H_9NO_3S_2$:
C, 53.59; H, 3.11; N, 4.81; S, 22.01
Found: C, 53.82; H, 3.08; N, 5.15; S, 21.71
The following Examples are for compounds also prepared by the procedures described the preparation of intermediates A and B and Example 55 above.

EXAMPLE 56

5-[(5-Methoxy-2-benzofuranyl)methylene]-2-thioxo-4-thiazolidinone mp 261°–263° (recrystallized from acetonitrile/N,N-dimethylformamide).

Calcd. for $C_{13}H_9NO_3S_2$:
C, 53.59; H, 3.11;N, 4.81; S, 22.01
Found; C, 53.68; H, 3.23; N, 4.87; S, 21.88.
The starting carboxylic acid was 5-methoxy-2-benzofurancarboxylic acid (W. B. Whalley, *J. Chem. Soc.*, 3479 (1953)).

EXAMPLE 57

5-[(Benzo[b]thien-2-yl)methylene]-2-thioxo-4-thiazolidinone mp 245°-dec (recrystallized from acetonitrile/N,N-dimethylformamide).

Calcd. for $C_{12}H_7NOS_3$;
C, 51.96; H, 2.54; N, 5.05; S, 34.68
Found: C, 51.87; H, 2.41; N, 5.13; S, 34.45.
The starting carboxylic acid was commercially available benzoylthiophene-2-carboxylic acid.

EXAMPLE 58

5-[[5-Methoxy-3-(1-methylethoxy)benzo[b]thien-2yl] methylene]-2-thioxo-4-thiazolidinone mp 242°-dec.

Calcd. for $C_{16}H_{15}No_3S_3$:
C. 52.58; H, 4.14; N, 3.83; S, 26.32
Found: C, 53.00; H, 4.13; N, 3.75; S, 25.95
The starting carboxylic acid was 3-(1-methylethoxy)-5-methoxy-benzo[b] thiophene-2-carboxylic acid (D. T. Connor, W. A. Cetenko, P. C. Unangst, and E. A. Johnson, U.S. Pat. No. 4,703,053.

EXAMPLE 59

5-[(5-Methoxy-1-phenyl-1-indol-2-yl) methylene]-2-thioxo-4-thiazolidinoine mp 250°–253° (recrystallized from aqueous acetonitrile/N,N-dimethylformamide).

Calcd. $C_{19}H_{14}N_2O_2S_2 \cdot 1H_2O$:
C, 59.35; H, 4.19; N, 7.29; S, 16.68
Found: C, 59.56; H, 4.03; N, 7.06; S, 16.02.
The starting carboxylic acid was 5-methoxy-1-phenyl-1H-indole-2-carboxylic acid (P. C. Unangst, D. T. Connor, S. R. Stabler, and R. J. Weikert, *J. Heterocyclic Chem.*, 24, 811 (1987)).

EXAMPLE 60

5-[(5-Methoxy-1-phenyl,1H-indol-2-yl)methylene]-2-thioxo-4thiazolidinone, 1-methylpiperidine salt A suspension of 3.0 g (0.0082 mole) of 5-[(5-methoxy-1-phenyl-1H-indol-2-yl) methylene]-2-thioxo-4-thiazolidinone in 50 ml of methanol was treated with 1.1 ml (0.89 g; 0.0090 mole) of 1-methylpiperidine. The mixture was stirred briefly on the steam bath until homogeneous and filtered warm. Cooling to room temperature overnight yielded 3.2 g (84% yield) of the crystalline, analytically pure salt, mp 188°–191°.

Calcd. for $C_{19}H_{14}N_2O_2S_2 \cdot C_6H_{13}N$:
C 64.48; H, 5.84; N, 9.03; S, 13.77
found: C, 64.02; H, 5.81; N, 882; S, 13.42.

EXAMPLE 61

5-[(5-Bromo-2-thienyl)methylene]-2-thioxo-4-thiazolidinone, monosodium salt

A suspension of 2.0 g (0.0065 mole) of 5-[(5-bromo-2thienyl) methylene]-2-thioxo-4-thiazolidinone in 25 ml of ethanol was treated with 3.3 ml of 2.00 N aqueous sodium hydroxide solution. The mixture was warmed on the steam bath until homogeneous and filtered warm. Cooling yielded 1.2 g (56% yield) of the analytically pure salt, mp 288°-dec.

Calcd. for $C_8H_3BrNOS_3Na \cdot 1.5\ H_2O$:

C 27.05; H, 1.70; N, .94

Found: C, 27.06; H, 1.66; N, 3.70.

EXAMPLE 62

5-[(3-Bromo-4-hydroxy-5-methoxyphenyl)methylene]-2-thioxo-4-thiazolidinone, disodium salt A suspension of 3.46 g (0.010 mole) of 5-[(3-bromo-4-hydroxy-5-methoxyphenyl) methylene]-2-thio in 50 ml of water was treated with 10.0 ml of 2.00 N aqueous sodium hydroxide solution. The mixture was warmed on the steam bath until nearly homogenous and filtered warm. The cooled filtrate was subjected to vacuum freeze-drying to leave a residue of 3.8 of red solid. The solid was digested briefly on the steam bath with 200 ml of acetone. Filtration gave 3.5 g (88% yield) of the analytically pure salt, mp> 310°.

Calcd. for $C_{11}H_6BrNO_3S_2Na_2V0.5\ H_2$ O:

C, 33.09; H, 1.77; N, 3.51

Found: C, 33.03; H, 1.73; N, 3.36.

EXAMPLE 63

5-[(4-Hydroxy,3,5-dimethoxyphenyl)methylene]-2,4-thiazolidinedione

Prepared according to the procedure described in Example 1 using 3,5-dimethoxy-4-hydroxybenzaldehyde (4.8 g, 26 mmoles) and 2,4-thiazolidinedione (2.9 g, 25 mmoles). Recrystallization from methanol gave the pure product (1.7 g), mp 248°–249° C.

EXAMPLE 64

5-[[3,5-(1,1)-dimethylethyl)-4-hydroxypheyl] methylene] 2,4-thiazolidinedione A mixture of 3,5-di-t-butyl-4-hydroxybenzaldehyde (6.5 g, 27 mmoles), 2,4-thiazolidinedione (3.0 g, 26 mmoles), sodium acetate (7.6 g, 93 mmoles), and acetic acid (40 ml) is stirred under an inert atmosphere and heated to reflux. After 78 hours the mixture is stirred into water (300 ml), and the precipitate is filtered off, rinsed three times with water, dried, and recrystallized from ethanol. The product is stirred in 1N NaOH (50 ml) and extracted several times with dichloromethane. The aqueous solution is acidified with acetic acid, stirred for 1–2 hours, and the precipitate is filtered off, rinsed three times with water and dried to afford the pure product (2.3 g), mp 238°–240° C.

The following compounds are prepared by the method described in Example 64:

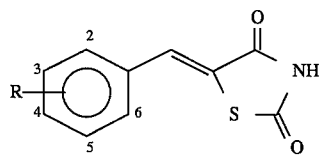

| Example | R | MP |
|---|---|---|
| 65 | H | 247–249 |
| 66 | 3-OMe | 197–198 |
| 67 | 4-OMe | 218–220 |
| 68 | 3-OMe, 4-OH | 225–227 |

INTERMEDIATE C

2-Thioxo-4-oxazolidinone

A solution of 72.9 g (0.75 mole) of potassium thiocyanate and 48.9 g (0.75 mole) of potassium cyanide in 85 ml of water was stirred in an ice bath and treated over 30 minutes with 60 ml (~0.80 mole) of 37% aqueous formaldehyde solution. The rate of addition was adjusted to maintain a reaction temperature of $<=10°$. The mixture was stirred for an additional 90 minutes, then treated over 1 hour with 156 ml of concentrated hydrochloric acid (reaction temperature maintained at <10°). The mixture was stirred for 16 hours as it slowly warmed to room temperature. The inorganic solids were filtered and discarded, and the filtrate was warmed on the steam bath for 90 minutes. The reaction mixture was again filtered, and the filtrate was extracted with ether (5X 200 ml). The combined extracts were dried (anhydrous sodium sulfate) and evaporated to an oil, which slowly crystallized. The solid was washed with hexane to yield 22.7 g (26% yield), mp 106°–109°. A sample recrystallized from ethyl acetate/hexane was analytically pure, mp 110°–112° (a mp of 113° is given by N. K. Ushenko and T. E. Gorizdra, *Ukrain. Khim. Zhur.*, 16, 545 (1950)).

EXAMPLE 69

5- [ ( 4-Hydroxy-3-methoxyphenyl )methylene ] -2-thioxo-4-oxazolidinone

A mixture of 3.25 g ( 0. 021 mole ) of 4-hydroxy-3-methoxybenzaldehyde, 2.34 g (0. 020 mole ) of 2-thioxo-4-oxazolidinone 5.8 g (0.071 mole) of sodium acetate and 15 ml of acetic acid was stirred and heated at reflux under a nitrogen atmosphere for 2 hours. The mixture was then stirred at room temperature for 16 hours, and added to 300 g of ice/water. The precipitated solid was filtered, washed with water, and recrystallized from aqueous methanol/N,N-dimethylformamide to yield 2.4 g (49% yield) of the oxazole product. A sample recrystallized a second time as above was analytically pure, mp 240°-dec. (A mp of 237°–238° is given by T. E. Gorizdra and S. N. Baranov, *Zhur. Obshchei Khim.*, 26, 3092 (1956)).

Calcd. fr $C_{11}H_9NO_4S \cdot 0.25H_2O$:

C, 51.65; H, 3.74; N, 5.48; S 12.54

Found: C 51.54; H, 3.97; N, 5.38; S, 12.17

Also prepared by the procedure described in Example 69, utilizing the appropriate aldehyde intermediate were:

EXAMPLE 70

5-[(3-Methoxyphenyl)methylene]-2-thioxo-4-oxazolidinone mp 215°-dec (recrystallized from methanol (N,N-dimethylformamide).

Calcd. for $C_{11}H_9NO_3S$:

C, 56.15; H, 386; N, 5.95; S 13.63

Found: C, 56.34, H, 3.87; N 5.95; S. 13.51

EXAMPLE 71

5-[(4-Methoxyphenyl)methylene]-2-thioxo-4-oxazolidinone mp 205°–207° (recrystallized from aqueous methanol/N, N-dimethylformamide). (A mp of 192° is given by N. K. Ushenko and T. E. Gorizdra, *Ukrain Khim. Zhur.*, 16, 545 (1950)).

Calcd. for $C_{11}H_9NO_3S$:

C. 56.15; H, 3.86; N, 5.95; S. 13.63 found: C, 56.10; H, 3.88; M. 6.03; S, 13.62.

EXAMPLE 72

5-[(3,4-Dimethoxyphenyl)methylene],2-thioxo-4-oxazolidinone mp 249°-dec.

Calcd. for $C_{12}H_{11}NO_4S$:

C, 54,32; H, 4.18; N, 5.28; S, 12.09

Found: C, 53.92; H, 4.10N, 5.22; S, 11.84.

EXAMPLE 73

5-[(4-Hydroxy-3,5-dimethoxyphenyl)methylene]2-thioxo-4-oxazolidinone mp 250°-dec. (recrystallized from aqueous acetonitrile/N, N-dimethylformamide).

Calcd. for $C_{12}H_{11}NO_5S$

C, 51.24; H, 3.94; N, 4.98:S, 11.40

Found: C, 51.00:H, 3.78;N, 5.30; S. 11.45.

EXAMPLE 74

5-[(4-Hydroxy-3,5-dimethylphenyl)methylene]-2-thioxo-4oxazolidinone mp 253°-dec.

Calcd. for $C_{12}H_{11}NO_3S$:

C, 57.81; H, 4.45; N, 5.62; S, 12.86

Found: C, 57.84; H, 4.49; N, 5.56; S, 12.54

EXAMPLE 75

5-[(3-Bromo-4-hydroxy-5-methoxyphenyl)methylene]-2-thioxo-4-oxazolidinone mp 260°–262°.

Calcd. for $C_{11}H_8BrNO_4S$:

C, 40.01; H, 2.44; N, 4.24; S, 9.71; Br, 24.20

Found: C, 40.18; H, 2.34; N, 4.07; S, 9.61; Br, 24.02.

EXAMPLE 76

2-Thioxo-5-[(2,4,5-trimethoxyphenyl)methylene]-4-oxazolidinone mp 265°-dec. (recrystallized from aqueous methanol/N, N-dimethylformamide).

Calcd. for $C_{13}H_{13}NO_5S$:

C, 52.87; H, 4.44; N, 4.74; S, 10.86

Found: C, 52.55; H, 4.30; N, 4.79; S, 10.47.

EXAMPLE 77

2-Thioxo-5-[(3,4,5-trimethoxyphenyl)methylene]-4-oxazolidinone mp 230°-dec. (recrystallized from aqueous methanol/N, Ndimethylformamide).

Calcd. for $C_{13}H_{13}NO_5S$:

C, 52.87; H, 4.44; N, 4.74; S 10.86

Found: C, 52.81; H, 4.32; N, 4.62; S, 10.39.

EXAMPLE 78

5-[(4-Hydroxy-3,5-dimethoxyphenyl)methylene]-2-thioxo-4-oxazolidinone, disodium salt A suspension of 3.1 g (0.011 mole) of 5-[(4-hydroxy-3, 5dimethoxyphenyl)methylene] -2-thioxo-4-oxazolidinone in 20 ml of water was treated with a solution of 11.0 ml of 2.00 N aqueous sodium hydroxide solution. The mixture was warmed briefly on the steam bath until nearly homogenous, then filtered warm. The cooled filtrate was subjected to vacuum freeze-drying to yield 3.5 g (98% yield) of the analytically pure salt product, mp >265°.

Calcd. for $C_{12}H_9NO_5SNa_2 \cdot 0.6\ H_2O$:

C, 42.89; H, 3.06; N, 4.17

Found: C, 42.67; H, 2.88; N, 4.00.

Also prepared by the above procedures was:

EXAMPLE 79

5-[(4-Hydroxy-3-methoxyphenyl)methylene]-2-thioxo-4-oxazolidinone, disodium salt mp >270°.

Calcd. for $C_{11}H_7NO_4SNa_2 \cdot 1\ H_2O$:

C, 42.18; H, 2.90; N, 4.47

Found: C, 41.84; H, 2.52; N, 4.37.

EXAMPLE 80

5-[(3,5-Dibromo-4-hydroxyphenyl)methylene]-2-thioxo-4-imidazolidinone

Prepared according to the procedure described in Example 1 using 3,5-dibromo-4-hydroxybenzaldehyde (4.5 g, 16 mmoles), 2-thiohydantoin (1.7 g, 15 mmoles), sodium acetate (4.5 g, 55 mmoles), and acetic acid (35 ml). Recrystallization from ethanol gave the pure product (1.4 g), mp 267° C. (dec).

EXAMPLE 81

5-[[4-hydroxy-3,5-bis(1-methylethyl)phenyl]methylene]-2-thioxo-4-imidazolidinone Prepared according to the procedure described in Example 1 using 4-hydroxy-3,5-bis(1-methylethyl)benzaldehyde (3.0 g, 15 mmoles), 2-thiohydantoin (1.6 g, 14 mmoles), sodium acetate (4.2 g, 51 mmoles), and acetic acid (35 ml), filtered off, dried, and recrystallized from acetonitrile to afford the pure product (1.4 g), mp 225°–230° C.

EXAMPLE 82

5-[{3-Bromo-4-hydroxyphenyl)methxlene]-2-thioxo-4-imidazolidinone

Prepared according to the procedure described in Example 1 using 3-bromo-4-hydroxybenzaldehyde (3.1 g, 15 mmoles), 2-thiohydantoin (1.7 g, 15 mmoles), sodium acetate (4.5 g, 55 mmoles), and acetic acid (35 ml), to afford the pure product (3.4 g), mp 262° C. (dec).

EXAMPLE 83

5-[[3,5-Bis(1,1-dimethylethyl)-4-hydroxyphenyl]methylene]-2-thioxo-4-imidazolidinone Prepared according to the procedure described in Example 1 using 3,4-di-t-butyl-4-hydroxybenzaldehyde (6.2 g, 26 mmoles), 2-thiohydantoin (2.9 g, 25 mmoles), sodium acetate (7.5 g, 91 mmoles), and acetic acid (40 ml). Heating under reflux is maintained for 36 hours. Recrystallization from acetonitrile gave the pure product (4.0 g), mp 279°–281° C. (dec).

EXAMPLE 84

5-[(2-Methoxyphenyl)methylene]-2-thioxo-4-imidazolidinone

A mixture of 2-methoxybenzaldehyde (2.5 g, 18 mmoles), 2-thiohydantoin (2.0 g, 17 mmoles), sodium acetate (4.0 g, 49 mmoles), acetic anhydride (μ ml), and acetic acid (15 ml) is stirred under an inert atmosphere and heated to reflux. After 1 hour the mixture is stirred into water (300 ml), and the precipitate is filtered off, rinsed with water three times and dried. The product is triturated in boiling methanol, filtered off, and dried to afford the pure product (3.4 g), mp 234°–235° C.

The following examples are prepared from the corresponding benzaldehydes using the procedure described in Example 84.

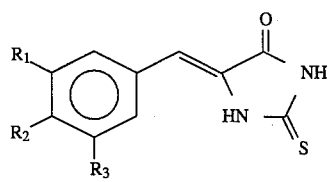

| Example | R₁ | R₂ | R₃ | mp °C. | Recryst. Solvent |
|---|---|---|---|---|---|
| 85 | OMe | H | H | 238–239 | MeOH |
| 86 | H | OMe | H | 266–267 | MeOH |
| 87 | OMe | OH | H | 237–238 | MeCN |

-continued

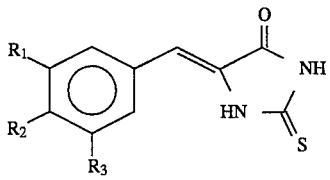

| Example | R₁ | R₂ | R₃ | mp °C. | Recryst. Solvent |
|---|---|---|---|---|---|
| 88 | OMe | OH | OMe | 268 (dec) | MeOH |

EXAMPLE 89

5-[[4-(Acetyloxy)-3-methoxyphenyl]methylene]-2,4-imidazoldinedione

Prepared according to the procedure described in Example 84, using 4-acetoxy-3-methoxybenzaldehyde (4.0 g, 21 mmoles) and hydantoin (2.0 g, 20 mmoles). Recrystallization from methanol/DMF gave the product (1.8 g), mp 275°–277° C., retaining 0.15 equivalents of DMF.

EXAMPLE 90

5-[(4-Hydroxy-3-methoxyphenyl) methylene]-2,4-imidazolidinedione

A mixture of 4-hydroxy-3-methoxybenzaldehyde (4.6 g, 30 mmoles), hydantoin (3.0 g, 30 mmoles), β-alanine (1.4 g, 16 mmoles), and acetic acid (40 ml) is stirred under an inert atmosphere and heated to reflux. After 4 hours the mixture is stirred into water (350 ml) and the precipitate is filtered off, rinsed successively with water (3X), ethanol (2X), and ether (2X), and dried. Recrystallization from methanol afforded the pure product (3.0 g), mp 272°–273° C.

EXAMPLE 91

5-[(3,5-Dimethoxy-4-hydroxyphenyl)methylene]-2,4-imidazolidinedione

Prepared according to the procedure described in Example 90 using 3,5-dimethoxy-4-hydroxybenzaldehyde (5.6 g, 30 mmoles), hydantoin (3.0 g, 30 mmoles), and μ-alanine (1.4 g, 16 mmoles), to afford the pure product (6.0 g), mp 296°–297° C.

EXAMPLE 92

5-[[3,5-Bis(1,1-dimethylethyl)-4-hydroxyphenyl]methylene]2,4-imidazolidinedione

A mixture of 3,5-di-t-butyl-4-hydroxybenzaldehyde (7.0 g, 30 mmoles), hydantoin (3.0 g, 30 mmoles), μ-alanine (1.4 g, 16 mmoles), and acetic acid (40 ml) is stirred under an inert atmosphere and heated to reflux. After 48 hours the mixture is stirred into water (300 ml), and the precipitate is filtered off, rinsed with water three times, and dried. Recrystallization from acetonitrile gave the pure product (4.8 g), mp 251°–252° C.

EXAMPLE 93

5-[(2-Methoxyphenyl)methylene]-3methyl-2,4imidazolodinedione

A mixture of 2-methoxybenzaldehyde (3.4 g, 25 mmoles), 3-methyl hydantoin (3.0 g, 21 mmoles), sodium acetate (6.0 g, 73 mmoles), acetic anhydride (3 ml), and acetic acid (20 ml) is stirred under an inert atmosphere and heated to reflux. After 15 hours the mixture is poured into water (200 ml), stirred, and the precipitate filtered off, rinsed three times with water and dried. Recrystallization from acetonitrile gave the pure product (3.1 g), mp 189°–190° C.

EXAMPLE 94

5-[(3-Methoxyphenyl)methylene]-3-methyl-2,4-imidazolidinedione

Prepared according to the procedure described in Example 93 using 3-methoxybenzaldehyde (3.5 ml, 28 mmoles) and 3-methyl hydantoin (3.0 g, 21 mmoles), to afford the product (3.6 g), mp 203°–205° C.

EXAMPLE 95

5-[(4-Methoxyphenyl)methylene]-3-methyl-2,4-imidazolidinedione

Prepared according to the procedure described in Example 93 using 4-methoxybenzaldehyde (3.4 g, 25 mmoles) and 3-methyl hydantoin (3.0 g, 21 mmoles). Recrystallization from acetonitrile gave the pure product (2.0 g), mp 221°–222° C.

EXAMPLE 96

5-[(4-Hydroxy-3-methoxyphenyl)methylene]-3-methyl-2,4-imidazolidinedione

Prepared according to the procedure described in Example 93 using 4-hydroxy-3-methoxybenzaldehyde (3.2 g, 21 mmoles) and 3-methyl hydantoin (3.0 g, 21 mmoles). Recrystallization from ethyl acetate gave the pure product (0.7 g), mp 227°–228° C.

EXAMPLE 97

5-[(3,5-Dimethoxy-4-hydroxyphenyl)methylene]-3-methyl-2,4-imidazolidinedione A mixture of 3,5-dimethoxy-4-hydroxybenzaldehyde (3.2 g, 18 mmoles), 3-methyl hydantoin (2.0 g, 18 mmoles), sodium acetate (6.0 g, 73 mmoles), acetic anhydride (3 ml), and acetic acid (25 ml) is stirred under an inert atmosphere and heated to reflux. After 72 hours the mixture is stirred into water (300 ml) and the precipitate is filtered off, rinsed three times with water and dried to give a product (4.0 g) which is a mixture of the desired product and its 0-acetate. A mixture of this product (2.1 g), sodium carbonate (3.5 g), DMSO (5 ml), and methanol (50 ml) is stirred and heated to reflux. After 18 hours the mixture is stirred into icewater (400 ml) and acidified with 4N HCl. The precipitate is filtered off, rinsed successively with water (3X), ethanol (2X), and ether (2X), and dried. Recrystallization from methanol/DMF gave the pure product (0.6 g), mp 269–°270° C.

EXAMPLE 98

5-[(3-Methoxyphenyl)methylene]-1-methyl-2,4-imidazolidinedione

A mixture of 2-methoxybenzaldehyde (3.8 g, 28 mmoles), 1-methyl hydantoin (3.0 g 26 mmoles), sodium acetate (8.4 g, 102 mmoles), acetic anhydride (10 ml), and acetic acid (40 ml) is stirred under an inert atmosphere and heated to reflux. After 24 hours the mixture is stirred into water (350 ml), stirred, and the resulting gum is isolated and washed by decantation, then crystallized from isopropanol. Recrystallization from acetonitrile gave the pure product (1.1 g), mp 195°–197° C.

EXAMPLE 99

5-[(4-Hydroxy-3-methoxyphenyl)methylene]-1-methyl-2,4imidazolidinedione

A mixture of 4-hydroxy-3-methoxybenzaldehyde (4.6 g, 30 mmoles), 1-methyl hydantoin (3.5 g, 30 mmoles), β-alanine (1.4 g, 16 mmoles), and acetic acid (40 ml) is stirred under an inert atmosphere and heated to reflux. After 8 hours the mixture is stirred into water (300 ml) and the precipitate filtered off, rinsed successively with water (3X), ethanol (2X), and ether (2X), and dried. Recrystallization from acetonitrile gave the pure product (1.1 g), mp 197°–198° C.

EXAMPLE 100

5-[(3,5-Dimethoxy-4-hydroxyphenyl)methylene]-1-methyl-2,4-imidazolidinedione Prepared according to the procedure described in Example 99 using 3,5-dimethoxy-4-hydroxybenzaldehyde (5.8 g, 31 mmoles) and 1-methyl hydantoin (3.5 g, 30 mmoles). Recrystallization from ethanol gave the pure product (2.8 g), mp 194°–196° C.

EXAMPLE 101

5-[(3,5-Dibromo-4-hydroxyphenyl)methylene]-1-methyl-2,4-imidazolidinedione

Prepared according to the procedure described in Example 99 using 3,5-dibromo-4-hydroxybenzaldehyde (8.4 g, 30 mmoles) and 1-methyl hydantoin (3.5 g, 30 mmoles) to afford the pure product (8.2 g), mp 271°–277° C.

EXAMPLE 102

5-[[4-Hydroxy-3,5-bis(1-methylethyl)phenyl]methylene]-1-methyl-2,4-imidazolidinedione Prepared according to the procedure described in Example 92 using 3,5-diisopropyl-4-hydroxybenzaldehyde (2.7 g, 13 mmoles) and 1-methyl hydantoin (1.4 g, 12 mmoles). Recrystallization from acetonitrile gave the pure product (0.4 g), mp 197°–208° C.

The following compounds are prepared according to the procedure described in Example 1 using appropriate corresponding starting materials.

EXAMPLE 103

5-[ (4-Pyridyl )methylene]
-2-thioxo-4-thiazolidinone, mp> 300°.

EXAMPLE 104

5- [ ( 2-Thienyl )methylene ]
-2-thioxo-4-thiazolidinone, mp 227°–229°.

EXAMPLE 105

5-[(5-Nitro-2-furanyl)
methylene-2-thioxo-4-thiazolidinone, mp
201°–202°.

EXAMPLE 106

5- [ ( 1-Phenyl-1H-indol-2-yl )methylene ]
-2-thioxo-4-thiazolidinone, mp 282°–283°.

EXAMPLE 107

5-[(3-Bromo-4-hydroxyphenyl)methylene]
-2-thioxo-4-oxazolidinone, mp 240°-(dec). Prepared
according to the procedure described in Example
69.

EXAMPLE 108

5-[[3,5-Bis(1,1-dimethylethyl-4-hydroxyphenyl]
methylene-2- thioxo-4-oxazolidinone A mixture of 14.1 g (0,060 mole) of 3,5-di-tert-butyl-4-hydroxybenzaldehyde, 7.0 g (0,060 mole) of 2-thioxo-4-oxazolidinone, 17.4 g (0.21 mole) of sodium acetate, and 75 ml of acetic acid is stirred and heated at reflux under a nitrogen atmosphere for 20 hours. The cooled reaction mixture is added to 900 g of ice/water and the precipitated product filtered and washed with water. There is obtained 16.2 g (81% yield) of the oxazole product, suitable for further reaction.

A sample of the above crude product is chromatographed over silica gel, using elution with 2.5% ethyl acetate in dichloromethane followed by 25% ethyl acetate. The chromatography product is recrystallized from aqueous acetonitrile to yield the analytically pure oxazole, mp 240° C. dec.

Calcd. for $C_{18}H_{23}NO_3S$:

C, 64.83; H, 6.95; N, 4.20

Found: C, 65.00H, 6.95; N, 4.17.

EXAMPLE 109

5-[[3,5-Bis{1,1-dimethylethyl-4-hydroxyphenyl]
methylene]-2,4-oxazolidinedione

A solution of 10.0 g (0,030 mole) of 5-[[3,5-bis (1,1-dimethylethyl-4-hydroxyphenyl]methylene-2-thioxo-4-oxazolidinone in 150 ml of tetrahydrofuran is cooled in treated with 4.2 ml (3.0 g, 0.030 mole) of triethylamine. The mixture is stirred with ice cooling for one hour, then treated with 10.0 ml (22.8 g, 0.16 mole) of iodomethane. The ice bath is removed and the mixture stirred for an additional 24 hours. The reaction mixture is filtered and the filter cake is washed several times with fresh tetrahydrofuran. The combined filtrates are evaporated and the residue is chromatographed (silica gel, 2% methanol in dichloromethane elution) to yield 4.4 g (42% yield) of the purified 2-methylthio-intermediate. This material is hydrolyzed without further purification.

A solution of 3.0 g (0.086 mole) of the above 2-methylthio-intermediate in 90 ml of ethanol is diluted with 30 ml of water and treated dropwise over 10 minutes with 5.0 ml of concentrated hydrochloric acid. The reaction mixture is stirred for 24 hours and the precipitated product is filtered and washed with hexane. The crude yield is 1.44 g (53%). A sample recrystallized from ethyl acetate/hexane yielded the analytically pure oxazolidinedione, mp 239° C. dec.

Calcd. for $C_{18}H_{23}NO_4$:

C, 68.12; H 7.31N, 4.41

Found: C, 68.22; H, 7.29; N, 4.05.

Also prepared by the above procedure, utilizing the appropriate 2-thioxo-4-oxazolidinone intermediate are:

EXAMPLE 110

5-[(4-Hydroxy-3,5-dimethoxyphenyl)methYlene]-2,
4-oxazolidine dione mp 268° dec. (recrystallized from acetonitrile/DMF/water)

Calcd. for $C_{12}H_{11}NO_6$:

C, 54.34; H, 4.18; N, 5.28

Found: C, 54.00; H, 4.17; N, 5.15.

EXAMPLE 111

5-[(4-Hydroxy-3,5-dimethylphenyl)methylene]-2,4-oxazolidinedione mp 275° C. dec. (recrystallized from acetonitrile/DMF/water).

Calcd. for $C_{12}H_{11}NO_4 \cdot 0.5H_2O$:

C, 59.50; H, 4.99; N, 5.78

Found: C, 59.31; H, 5.02; N, 5.72.

EXAMPLE 112

5-[[3,5-Bis(1,1-dimethylethyl)-4-hydroxyphenyl]
methYlene]-2-thioxo-4-oxazolidinone, choline salt A solution of 2.45 g (0.0069 mole) of 46.6% aqueous choline bicarbonate in 50 ml of methanol is stirred and treated over 5 minutes with 2.31 g (0.0069 mole) of 5[3,5-bis(1,1-dimethylethyl)-4-hydroxyphenyl] methylene]-2-thioxo-4-oxazolidinone. The reaction mixture is warmed for a few minutes to reflux on the steam bath, and filtered hot. The cooled filtrate is evaporated, and the residue recrystallized from acetone/tert-butyl methyl ether to yield 2.1 g (70% yield) of the analytically pure choline salt, mp 167° dec.

Calcd. for $C_{23}H_{36}N_2O_4S$:

C, 63.27; H, 8.31; N, 6.42

Found: C, 63.22; H, 8.21; N, 6.28

EXAMPLE 113

5-[[3,5-bis(1,1-dimethylethyl)-4-hydroxYPhenYl]
methYlene]-2,4-thiazolidinedione, choline salt A solution of 46.6% aqueous choline bicarbonate (10.55 g, 29.8 mmoles) is added dropwise under nitrogen to a stirred suspension of 5-[[3,5-bis(1,1-dimethylethyl)-4hydroxyphenyl] methylene)2,4-thiazolidinedione (10.0 g, 30.0 mmoles) in ethanol (100 ml). The solution is gradually warmed to reflux for one hour, and is then cooled and stripped of solvent by rotary evaporator. Two 50-ml portions of ethanol are successively mixed with and stripped from the residue which is then thoroughly dried under vacuum. The residue is triturated in diethyl ether, filtered off, washed twice with ether, and dried under vacuum at 80° C. overnight to afford the crystalline choline salt (12.8 g), mp 215° C. dec.

Calcd. for $C_{18}H_{22}NO_3S \cdot C_5H_{14}NO$:

C, 63.27; H, 8.31; N, 6.42

Found: C, 63.12; H, 8.28; N, 6.17

The usefulness of the compounds of the present invention as inhibitors of histamine release is demonstrated by the following assay. The assay is essentially as generally accepted among the ordinarily skilled artisans to show activity having usefulness to treat the diseases or conditions as set out in the present invention. A description of the procedure follows.

HISTAMINE RELEASE FROM HUMAN BASOPHILS (hereinafter HHB )

The HHB assay quantitates active histamine release, and its inhibition by drugs, from basophils of human blood. Thus, the assay provides evaluation of the compounds of formula I for treating the conditions or diseases as is the present invention. As described herein the assay includes modifications of the method described by R. P. Siraganian in "An Automated Continuous-Flow System for the Extraction and Fluorometric Analysis of Histamine", Anal. Biochem., 57, 383–394 (1974 ).

METHODS

Preparation of Leukocytes

Blood is drawn from allergic donors (chosen on the basis of adequate histamine release induced by a challenge), using standard venipuncture methods, into Vacutainers with EDTA in water as anticoagulant. The blood samples are placed briefly on a rotary mixer. The blood is mixed with Hespan (hydroxy ethyl starch, 0.5 ml per 1.0 ml of blood), the tube inverted several times to mix and then left undisturbed at room temperature until a sharp separation is observed between the settled red cells and the leukocyte and platelet-rich plasma. This usually occurs within 35–45 minutes.

The plasma fraction is removed and centrifuged for 12 minutes at 4° C. at 1050 RPM (100 Xg). The platelets remain in the plasma and are discarded. The pelleted leukocytes are shaken gently to disrupt the cell button and washed twice with HA buffer containing 0.005 M EDTA and resuspended in HACM buffer to approximately one-quarter the original blood volume. A sample is prepared for Hematology, where a total white blood cell and platelet count is done using a Coulter Counter.

Protocol Design

Aliquots (0.1 ml) of cells are added to triplicate assay tubes containing 0.4 ml of either 6% perchloric acid (for total histamine content), vehicle control (for spontaneous release), or drug. The tubes are incubated at room temperature for 8 minutes, and then placed in a 37° C. water bath for 2 more minutes. Buffer or challenge agents (at 37° C.) are added to the tubes and they are incubated for an additional 45 minutes at 37° C. in a shaking water bath. The tubes are then spun at 2000 RPM (1200 g) for 3 minutes to pellet the cells and the supernatants are removed and assayed for histamine by the fluorometric method.

Drug Preparation

A 300 µM stock solution of each test compound is prepared in distilled water, using 0.5 ml DMSO/100 ml and/or 0.2 ml of 1N NaOH or HCl and/or heat to aid in dissolution. Five ml of the stock solution is diluted (1:2) with 5 ml of two times concentrated HACM buffer to yield the stock working concentration of 150 µM. When added to the cells and stimulus, a final test concentration of 100 µM drug results. Further dilutions are made with HACM buffer for 33, 10, 3.3, 1.0 µM, etc.

Challenge Agent Preparation

Short ragweed and house dust extracts (Greer Laboratories, Inc.) are supplied as aqueous extracts in stock concentrations of 40,000 and 10,000 protein nitrogen units per milliliter (PNU/ml), respectively. Aqueous solutions of anti-IgE antisera (rabbit-raised antibody) are purchased from Dako via Accurate Chemicals. The aqueous solutions of ragweed, house dust, and anti-IgE are diluted 1:2 with two times concentrated HACM and then further diluted with HACM to yield final stock concentrations of 6000 PNU/ml for ragweed and house dust and 1:50 dilution for the anti-IgE antisera. Further dilutions for working solutions are made in HACM buffer. All stock and working solutions are stored at 4° C. Working solutions comprise ⅙ of the final volume in the cell reaction, therefore, working solutions of challenge agents are made up six times the required final concentration.

In each experiment, cells are challenged according to the previously determined sensitivity of that donor to the particular challenge agent. Short ragweed and house dust concentrations are expressed in PNU/ml, and anti-IgE antisera is expressed as dilutions, e.g., IE-5 (1:100,000), 3E-5 (1:30,000), and IE-4 (1:10,000).

Calculation and Interpretation of Results

The total histamine concentration in the "total" (acid-treated) samples must be 15 ng/ml to be acceptable. Spontaneous release of histamine from the cells should not exceed 15% of the total histamine, and is frequently <5%. The maximum percentage histamine released varies with the donor. The net amount released by the challenge agent must exceed 25% of the total cellular histamine to confidently assess inhibition by test compounds. Spontaneous histamine release is subtracted from both "totals" and challenged cells to calculate net percent release. Percent inhibition is shown in the Table and is calculated using the following formula:

$$1 - \left[ \frac{\text{Mean net \% release treated samples}}{\text{Mean net \% release for challenged control}} \right] \times$$

$$100 = \% \text{ inhibition}$$

TABLE

| Ex | $R_1$ | $R_2$ | $R_3$ | $R_4$ | $R_5$ | HHB % Inhibition of Histamine Release at 33 μM |
|---|---|---|---|---|---|---|
| 1 | MeO | MeO | H | H | H | * |
| 2 | MeO | H | OMe | H | H | * |
| 3 | MeO | H | H | OMe | H | 86 |
| 4 | MeO | OMe | OMe | H | H | * |
| 5 | MeO | H | OMe | OMe | H | 73 |
| 6 | H | OMe | OMe | OMe | H | 92 |
| 7 | Cl | H | Cl | H | H | 81 |
| 8 | H | Cl | Cl | H | H | 88 |
| 9 | H | OMe | OMe | H | H | 84 |
| 10 | H | OMe | OH | OMe | H | 90 |
| 11 | H | F | OMe | H | H | 94 |
| 12 | H | OH | OH | H | H | 41 |
| 13 | H | Br | OH | H | H | 61 |
| 14 | H | Br | OH | Br | H | * |
| 15 | H | Me | OH | Me | H | 84 |
| 16 | H | OMe | OH | Br | H | 51 |
| 17 | H | H | H | H | H | 39 |
| 18 | MeO | H | H | H | H | * |
| 19 | H | MeO | H | H | H | 100 |
| 20 | H | H | MeO | H | H | 90 |
| 21 | H | OH | H | H | H | 75 |
| 22 | H | H | OH | H | H | 95 |
| 23 | H | OEt | H | H | H | * |
| 24 | H | OCHMe$_2$ | H | H | H | * |
| 25 | H | OCH$_2$Ph | H | H | H | * |
| 26 | H | Me | H | H | H | 58 |
| 27 | H | CF$_3$ | H | H | H | 58 |
| 28 | H | Cl | H | H | H | * |
| 29 | H | Br | H | H | H | * |
| 30 | H | NO$_2$ | H | H | H | * |
| 31 | H | H | Cl | H | H | 95 |
| 32 | H | H | Br | H | H | 61 |
| 33 | H | H | OPh | H | H | 64 |
| 34 | H | H | NO$_2$ | H | H | * |
| 35 | H | H | SMe | H | H | * |
| 36 | H | MeO | OH | H | H | 79 |
| 37 | H | MeO | H | MeO | H | 80 |
| 38 | H | H | Me | H | H | 30 |
| 39 | H | H | Ph | H | H | 28 |
| 40 | Cl | Cl | H | H | H | 60 |
| 41 | Cl | H | H | H | Cl | * |
| 43 | H | F | H | H | H | * |
| 44 | OH | H | H | H | H | * |
| 45 | H | OH | OMe | H | H | 59 |
| 47 | H | OH | OMe | OMe | H | 79 |
| 48 | OMe | H | H | H | OMe | * |
| 49 | OH | H | H | OMe | H | 98 |
| 50 | H | OH | H | OMe | H | 96 |
| 51 | H | OMe | OH | tBu | H | 34 |
| 52 | OH | H | OMe | OMe | H | 79 |
| 53 | H | Me$_2$NCH$_2$ | OH | MeO | H | * |
| 54 | | | | | | 85 |
| 55 | | | | | | 88 |
| 56 | | | | | | 26 |
| 57 | | | | | | 66 |
| 58 | | | | | | 24 |
| 59 | | | | | | 72 |
| 103 | | | | | | 95 |
| 104 | | | | | | 87 |
| 105 | | | | | | 88 |
| 106 | | | | | | 84 |
| 63 | H | MeO | OH | MeO | H | 60 |
| 64 | H | tBu | OH | tBu | H | 49 |
| 65 | H | H | H | H | H | * |
| 66 | H | OMe | H | H | H | 92 |
| 67 | H | H | OMe | H | H | 90 |
| 68 | H | OMe | OH | H | H | 81 |
| 69 | H | MeO | OH | H | H | 77 |
| 70 | H | MeO | H | H | H | 58 |
| 71 | H | H | MeO | H | H | 83 |
| 72 | H | MeO | MeO | H | H | 43 |
| 73 | H | MeO | OH | Meo | H | 89 |
| 74 | H | Me | OH | Me | H | 88 |
| 75 | H | Br | OH | MeO | H | * |
| 76 | MeO | H | MeO | MeO | H | * |
| 77 | H | MeO | MeO | MeO | H | 76 |
| 107 | H | Br | OH | H | H | 66 |
| 80 | H | Br | OH | Br | H | 85 |
| 82 | H | Br | OH | H | H | 78 |
| 83 | H | tBu | OH | tBu | H | 30 |
| 84 | OMe | H | H | H | H | * |
| 85 | H | OMe | H | H | H | 28 |
| 86 | H | H | OMe | H | H | * |
| 87 | H | OMe | OH | H | H | * |
| 88 | H | OMe | OH | OMe | H | 68 |
| 89 | H | MeO | AcO | H | H | 27 |
| 90 | H | MeO | OH | H | H | * |
| 91 | H | MeO | OH | MeO | H | * |
| 92 | H | tBu | OH | tBu | H | 11 |

TABLE-continued

| Ex | $R_1$ | $R_2$ | $R_3$ | $R_4$ | $R_5$ | HHB % Inhibition of Histamine Release at 33 μM |
|---|---|---|---|---|---|---|

Structure with $R_1$, $R_2$, $R_3$, $R_4$, $R_5$ on benzene ring, with CH=C(NHC(O)Me)C(O)N—Me side chain:

| Ex | $R_1$ | $R_2$ | $R_3$ | $R_4$ | $R_5$ | |
|---|---|---|---|---|---|---|
| 93 | MeO | H | H | H | H | * |
| 94 | H | MeO | H | H | H | * |
| 95 | H | H | MeO | H | H | * |
| 96 | H | MeO | OH | H | H | 58 |
| 97 | H | Meo | OH | MeO | H | 51 |

Structure with $R_1$–$R_5$ on benzene ring, with CH=C(N(Me)C(O)NH)C(O) side chain:

| Ex | $R_1$ | $R_2$ | $R_3$ | $R_4$ | $R_5$ | |
|---|---|---|---|---|---|---|
| 98 | H | MeO | H | H | H | * |
| 99 | H | MeO | OH | H | H | 92 |
| 100 | H | MeO | OH | MeO | H | 68 |
| 101 | H | Br | OH | Br | H | 96 |

*Indicates not active at 33 μM.
E Enhanced release at this concentration.
MeO is methoxy.
OCHMe$_2$ is isopropoxy.
OCH$_2$Ph is benzyloxy.
tBu is tertiarybutyl.
Me$_2$NCH$_2$ is dimethylamine.

Activity is measured as % inhibition of histamine release from human basophils challenged with anti-IgE at a 33 μM concentration of drug.

The IC$_{50}$ is calculated to give the μM necessary to provide 50% inhibition.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmunoassay (RIA) kits of LTB$_4$ and PGF$_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; Na$_2$HPO$_4$, 1.15 g; KH$_2$PO$_4$ 0.2 g; and KCl, 0.2 g/l). Cells are finally suspended in PBS containing 1.0 mM calcium at a density of 2×10$^6$ cells/ml. Cells are incubated with and without test agent (in DMSO) (1% DMSO is without effect on arachidonic acid metabolism) for ten minutes at room temperature. Calcium ionophore A23187 (5 μM) is added and cells are incubated for seven minutes at 37° C. The reaction is stopped by chilling the tubes on ice for ten minutes. Cells are separated by centrifugation and the supernatant is stored at −20°. Aliquots (100 μl) are analyzed for LTB and PGF$_{2\alpha}$ using radioimmunoassay kits as provided by the supplier.

Table 1 contains biochemical data obtained from this whole cell assay as IC$_{50}$S which are calculated as the amount of test compound causing 50% inhibition of LTB$_4$ or PGF$_{2\alpha}$ formation.

Carrageenan-Induced Rat Foot Paw Edema-2 (CEF-2) Assay: Protocol

Carrageenan solution (1% w/v) is prepared by dissolving 100 mg carrageenan (Marine Colloidal Div., Springfield, N.J.) in 10 ml of sterile saline (0.9%) solution (Travenol). The solution is vortexed for 30 to 45 minutes. Animals are dosed with compound one hour before carrageenan challenge. Foot paw edema is induced by injecting 0.10 ml of the 1% carrageenan subcutaneously into the plantar portion of the right hind paw of each rat under light anesthesia. Initial foot paw volume is measured immediately following carrageenan challenge using mercury plethysmography (Buxco Electronics). Edemia is measured five hours after carrageenan. The difference between the five-hour and the initial paw volume is expressed as delta edema. The delta edema for each test group of animals is used to calculate the percent inhibition of edema achieved by the compound at the test dose compared with the vehicle control group. The ID$_{40}$ (the dose at which swelling is inhibited by 40%) is calculated by probit analysis for the dose at which 40 percent inhibition occurs.

TABLE II

| Example No. | ARBL[1] | ARBC[2] | CFE[3] |
|---|---|---|---|
| 64 | 100 | 95 | 31.8 (1) |
| | | | 39.8 (3) |
| | | | 53.7 (10) |
| | | | 58.8 (30) |
| 108 | 92 | 86 | 44.1 (1) |
| | | | 41.1 (3) |
| | | | 32.1 (10) |
| | | | 40.4 (30) |
| 109 | 95 | 89 | 18.5 (1) |
| | | | 23.5 (3) |
| | | | 36.8 (10) |
| | | | 39.4 (30) |
| 110 | 67 | N[4] | |
| 32 | 93 | 59 | |

[1] Percent inhibition of cellular 5-lipoxygenase at 16 μM.
[2] Percent inhibition of cellular 5 cyclooxygenase at 16 μM.
[3] Percent inhibition of carrageenan footpad edema (CFE) test at various doses (mg/kg) of test drug.
[4] N inactive at screening concentration.

Accordingly, the present invention also includes a pharmaceutical composition for treating one of the above diseases or conditions comprising an antidisease or anticondition effective amount of a compound of the formula I as defined above together with a pharmaceutically acceptable carrier.

The present invention further includes a method for treating one of the above named diseases or conditions in mammals, including man, suffering therefrom comprising administering to such mammals either orally or parenterally, preferably oral, a corresponding pharmaceutical composition containing a compound of formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 1 to 50 mg according to the particular application and the potency of the active ingredient. The compositions can, if desired, also contain other compatible therapeutic agents.

In therapeutic use as described above, the dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

In addition to the compounds of formula I, the pharmaceutical compositions can also contain other active ingredients, such as cyclooxygenase inhibitors, nonsteroidal anti-inflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
 (1) the propionic acid derivatives;
 (2) the acetic acid derivatives;
 (3) the fenamic acid derivatives;
 (4) the biphenylcarboxylic acid derivatives; and
 (5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free -CH(CH₃)COOH or -CH₂CH₂COOH group (which optionally can be in the form of a pharmaceutically acceptable salt group, e.g., -CH(CH₃)COO⁻Na⁺ or -CH₂CH₂COO⁻Na⁺ ), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

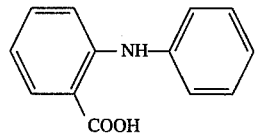

which can bear a variety of substituents and in which the free -COOH group can be in the form of a pharmaceutically acceptable salt group, e.g., -COO⁻Na⁺.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

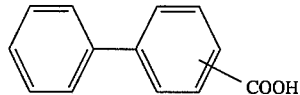

which can bear a variety of substituents and in which the free -COOH group can be in the form of a pharmaceutically acceptable salt group, e.g., -COO-Na⁺.

The oxicams which can be used in the present invention comprise: piroxicam, sudoxicam, isoxicam, and 4-hydroxyl-1,2benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesic/nonsteroidal antiinflammatory drugs which have the general formula:

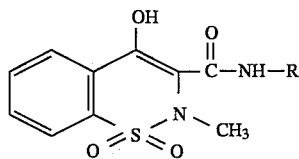

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acidd, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclose din U.S. Pat. No. 4,237,160. They may also contain histidine decarboxylase inhibitors such as α-fluoromethylhistidine, described in U.S. 4,325,961. The compounds of formula I may also be advantageously combined with an H₁ or H ₂-receptor antagonist, such as for instance cimetidine, ranitidine, terfenadine, famotidine, temelastine, acrivastine, loratidine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a K⁺/H⁺ATPase inhibitor such as omeprazole, disclosed in U.S. Pat. No. 4,255,431, and the like. Each of the references referred to in this paragraph is hereby incorporated herein by reference.

Thus, "acetic acid derivatives" as defined herein are nonnarcotic analgesics/nonsteroidal antiinflammatory drugs having a free -CH₂COOH group (which optionally can be in the form of a pharmaceutically acceptable salt group, e.g., -CH₂COO⁻Na⁺), typically attached directly to a ring system, preferably to an aromatic or heteroaromatic ring system.

We claim:

1. A method of treating inflammation in humans comprising administering an anti-inflammatory amount of a compound of the formula (I)

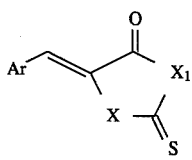

and the pharmaceutically acceptable salts thereof; wherein Ar is (i) phenyl;

(ii) phenyl substituted by from one to three of lower alkoxy, hydroxy, halogen, trifluoromethyl, $NO_2$, mercapto, or lower alkylthio, $NR_{10}R_{11}$ wherein $R_{10}$ and $R_{11}$ are independently hydrogen, or lower alkyl;

X is NH or $NCH_3$; and $X_1$ is NH or $NCH_3$.

2. The method of claim 1 wherein $X_1$ is NH.

3. The method of claim 1 wherein X is NH.

4. The method of claim 1 wherein $X_1$ is $NCH_3$ and X is NH.

5. The method of claim 1 wherein the compound is 4-imidazolidinone, 5-[ (3, 5-dibromo-4-hydroxyphenyl) methylene] -2-thioxo-;

4-imidazolidinone, 5-[ (3-bromo-4-hydroxyphenyl) methylene ] -2-thioxo-;

4-imidazolidinone, 5-[ (2-methoxyphenyl)methylene] -2-thioxo-;

4-imidazolidinone, 5-[ (3-methoxyphenyl )methylene ] -2-thioxo-;

4-imidazolidinone, 5-[ (4-methoxyphenyl) methylene] -2-thioxo-; and 4-imidazolidinone, 5- [ (4-hydroxy-3,5-dimethoxyphenyl) methylene] -2- thioxo-.

* * * * *